United States Patent

Danz

[11] 4,272,910
[45] Jun. 16, 1981

[54] OCULAR PROSTHETIC OR THE LIKE

[76] Inventor: William R. Danz, 87 Park Ave., Glen Rock, N.J. 07452

[21] Appl. No.: 164,943

[22] Filed: Jul. 10, 1980

Related U.S. Application Data

[63] Continuation-in-part of Ser. No. 62,329, Jul. 31, 1979, abandoned.

[51] Int. Cl.³ .................. A63H 33/26; A63H 3/38; A61F 1/16
[52] U.S. Cl. ............................................ 46/45; 3/13; 46/165
[58] Field of Search .................. 3/13; 46/45, 165, 170; 35/17

[56] References Cited

U.S. PATENT DOCUMENTS

| | | | |
|---|---|---|---|
| 1,763,312 | 6/1930 | Marcus | 46/165 |
| 3,480,971 | 12/1969 | Smith | 3/13 |
| 3,846,199 | 11/1974 | Cappelli | 3/13 X |
| 3,905,130 | 9/1975 | Gordon et al. | 46/165 X |

Primary Examiner—Ronald L. Frinks
Attorney, Agent, or Firm—Hopgood, Calimafde, Kalil, Blaustein & Judlowe

[57] ABSTRACT

The invention contemplates an artificial eye which in its preferred form is completely self-contained and embodies a simulated iris, with the appearance of a pupil which will dilate in response to a photoelectrically detected reduction in environmental light. Various embodiments are described.

26 Claims, 9 Drawing Figures

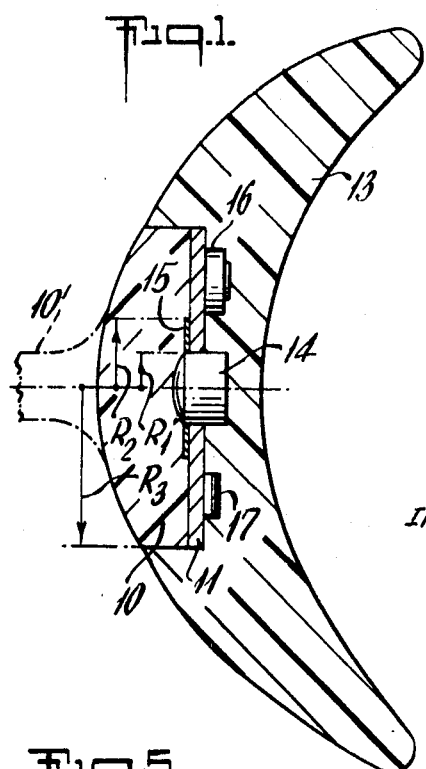
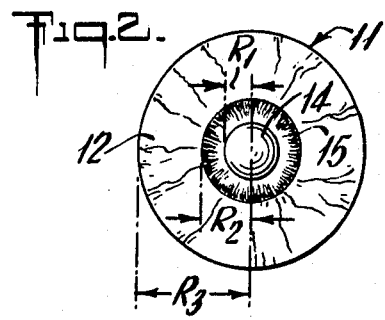
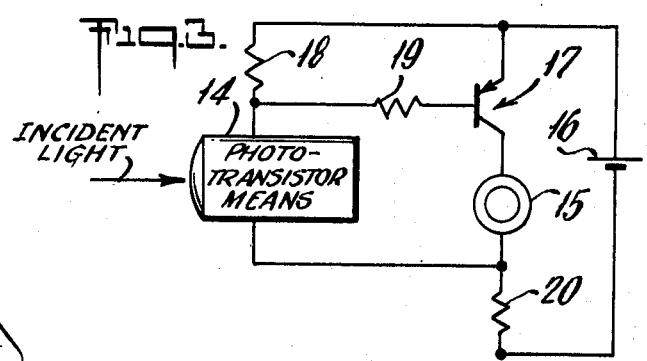
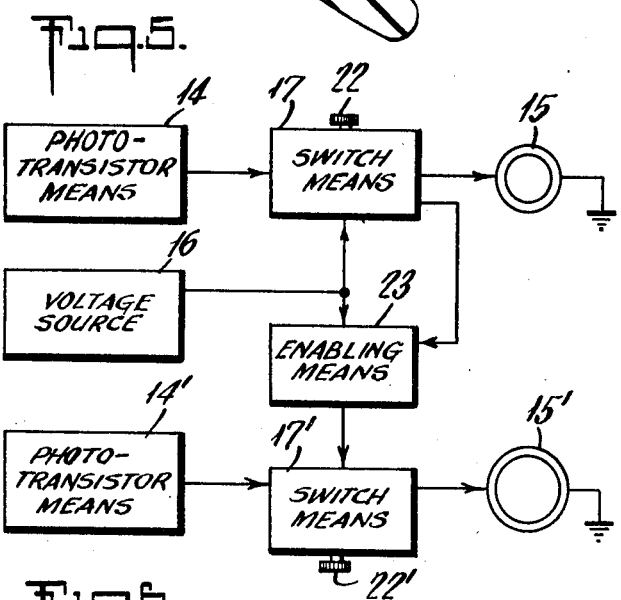
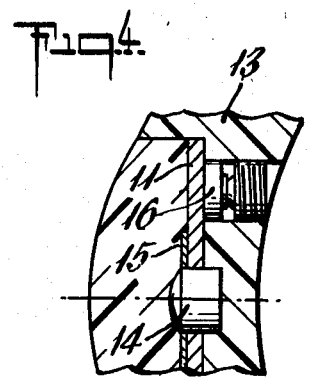
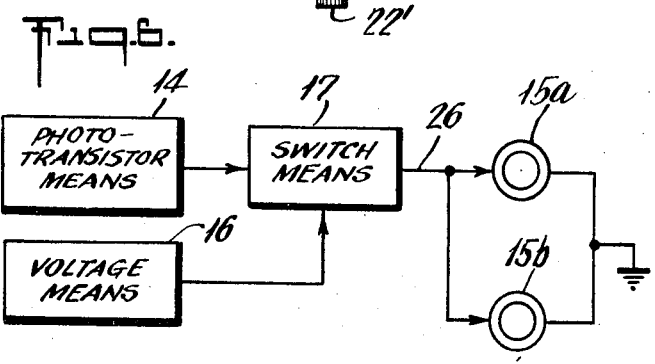
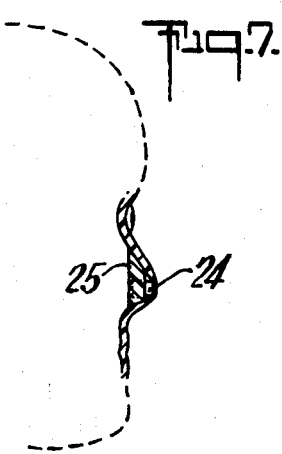

OCULAR PROSTHETIC OR THE LIKE

BACKGROUND OF THE INVENTION

This application is a continuation-in-part of my copending application Ser. No. 062,329, filed July 31, 1979, now abandoned.

The invention relates to an artificial eye construction having application as an ocular prosthetic for humans who have lost an eye, as well as for other purposes such as doll's eyes.

The fabrication of ocular prosthetics has developed to an advanced art wherein emphasis has been placed on so faithfully reproducing color, striations, vein markings and the like that the artificial member can be distinguished from the patient's surviving natural eye, essentially only by observing the eyes under changing environmental-light conditions. So far as I am aware, no artificial eye exists or has been proposed in which the simulated pupil is caused to dilate in a weakend light environment.

BRIEF STATEMENT OF THE INVENTION

It is accordingly an object of the invention to provide an improved artificial eye having the appearance feature of a pupil which dilates upon reduction of the intensity of environmental light.

A specific object is to achieve the foregoing object using electrically sensed and electrically controlled means.

Another specific object is to provide a completely self-contained self-operating artificial eye of the character indicated.

It is also a specific object to achieve the above objects with a structure wherein at least two differently dilated pupil conditions are simulated in substantially correct correlation with the operation of the natural eye.

A further object is to meet above objects in the context of doll's eyes, specifically achieving coordinated pupil-dilation at both eyes.

A general object is to meet the above objects with basically simple and light-weight structure which places no undue burden upon the patient, and which lends itself to incorporation in the context of iris coloring and design unique to the patient.

The foregoing objects and other features of novelty and invention are achieved, in a preferred form, by embedding in a plastic potting a circuit board and its electrical components, the circuit board having iris indicia on the front face thereof and with a photoelectric device such as a phototransistor mounted within a pupilary area of minimum size, being the simulation of pupil size at maximum brightness of the environment. Surrounding this minimum-area pupil, and in front of the iris indicia, electro-optical means such as a liquid-crystal element is mounted, the same having an effective area such that when excited to block light transmission (i.e., to appear dark), the pupil appears to have been dilated. The electric-circuit connections are such that the liquid-crystal element is excited when the photoelectric means detects a predetermined drop in environmental light intensity, and the reverse operation applies when the light environment again becomes sufficiently bright.

DETAILED DESCRIPTION

The invention will be illustratively described for a preferred form and for several modifications, all in conjunction with the accompanying drawings, in which:

FIG. 1 is an enlarged simplified vertical sectional view showing a preferred form of an ocular prosthetic of the invention;

FIG. 2 is a simplified view in elevation of iris indicia incorporated in the prosthetic of FIG. 1;

FIGS. 3, 3A and 3B are different electric-circuit diagrams for components of FIG. 1;

FIG. 4 is a fragmentary sectional view to show a modification of FIG. 1;

FIG. 5 is an electrical block diagram to illustrate circuit components for a modification of FIG. 1;

FIG. 6 is a further electrical block diagram, to show application of the invention to coordinated dilation of both eyes of a doll; and FIG. 7 is a fragmentary profile of the face of a doll in which apparatus of FIG. 6 is incorporated.

Figure 3A:
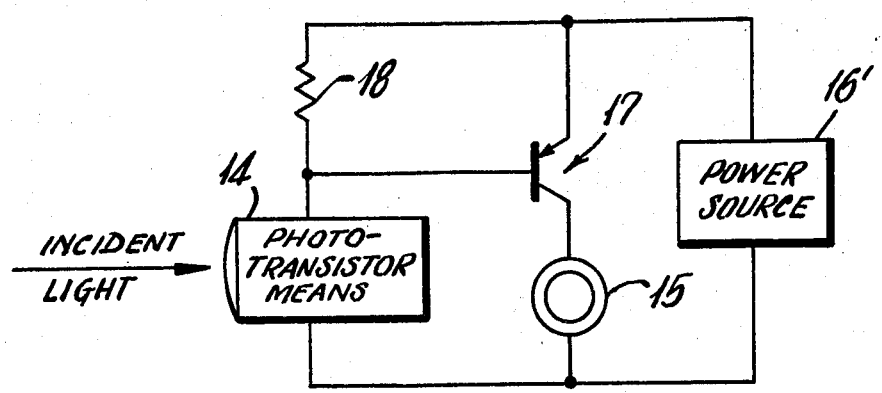

In FIG. 1, the invention is shown in application to an artificial eye comprising a central front body portion 10 of transparent light-transmitting plastic potting material such as clear methylmethacrylate, to the inner base of which a circular panel 11 has been bonded. Panel 11 may be a printed-circuit board of radius $R_3$ corresponding to the outer diameter (generally 12 mm) of the iris for the eye, iris indicia 12 being inscribed in or carried by the front face of board 11, as suggested in FIG. 2, so that indicia 12 are clearly observable via the clear body region 10 as to color, striations, and other markings which preferably match the other eye (the so-called good eye) of the patient. The body of the eye is completed by further molded contours of a white plastic material 13 such as methylmethcrylate pigmented as with zinc oxide, to simulate the sclera of the eye, with the result that board 11 and all other internal components become fully embedded within the plastic body.

In the preferred form shown, the board 11 is annular, having a central hole of radius $R_1$, sized to simulate the radius of a pupil in a bright-light environment. A phototransistor 14, which may be contained in a lensed-window, miniature, hermetic cylindrical package, is mounted to board 11 at this central opening, the lensed-window end facing forward as suggested by a bowed contour in FIG. 1. The phototransistor is thus at all times directly exposed to environmental-light conditions, via the clear body portion 10.

Immediately surrounding the phototransistor 14 and at the radially inner margin of the front face of the iris indicia 12 is an annulus 15 of electro-optically sensitive material, sometimes known as a liquid-crystal display (LCD); the inner radius of the annular element 15 is substantially identical to the outer radius $R_1$ of the phototransistor (14) or small-pupil simulating area, while the outer radius $R_2$ of annulus 15 is of proportion to enable simulation of the outer diameter of a pupil that has been dilated due to a light environment of intensity less than the bright environment.

It will be understood that the annular display 15 is a thin sandwich of front-to-back assembled thin layers involving liquid crystals between conductive plates which are respectively covered with vertical and horizontal polarizer coatings. It suffices merely to explain that when a suitable voltage is applied to the sandwich plates, the liquid crystals become untwisted, enabling the polarizers to block passage of incident light to the reflective coating, so that the display 15 appears black; when unexcited, the electric field between the plates no longer acts on the crystals, which therefore revert to their 90-degree light-twisting state, wherein light passes through both polarizers and the sandwich appears transparent, so that the iris color and markings are visible all the way radially inward to the central darkened area of phototransistor 13. Cooperating further components are mounted to and may be interconnected at the back side of board 11; in FIG. 1, these are shown as a single-cell voltage source 16 and electric-switch means such as a suitable transistor 17.

The complete electrical circuit of described and further elements is shown in FIG. 3, it being understood that all electrical components are fully potted and embedded in the body 10-13 of the eye of FIG. 1. In operation, light of sufficient intensity (bright light) hits phototransistor 14, which is thereby turned on, drawing current through resistors 18 and 19. Current thus drawn from the base of transistor 17 (switching means) insures that transistor 17 will remain turned off, so that no current flows out of the emitter of transistor 17; in this way, for the stated bright-light condition, no current can flow through the electro-optical means 15, which therefore remains transparent, revealing iris indicia down to radius $R_1$. When light intensity reduces, the phototransistor means 14 changes to its off state, thus precluding current flow through means 14 via the base of transistor 17; in this state, current flow is via resistors 18-19 in series to the base of transistor 17, with the result that transistor 17 is turned on and current flows out of the emitter of transistor 17 and through the annulus 15. The excited annulus 15 blocks light transmission, and the pupil appears to have been enlarged, to the incremental extent of the area of annulus 15. When the bright-light environment returns, the phototransistor 14 again turns on, and the described events repeat whenever light intensity passes through the level predetermined for switch action.

FIG. 4 shows a modification wherein the battery 16 is removably held in place in contact with the printed circuit board, by means of a removable plug 21, threaded into the local bore of body 13 in which battery 16 is inserted. Operation is otherwise as described for FIG. 1.

FIG. 5 is a block diagram of a modification in which already described elements are given the same reference numbers. Thus, voltage from source 16 will be supplied to excite annulus 15 only if phototransistor means 14 is turned off by reason of reduction in light intensity to and below a predetermined level. A manual adjustment at 22 will be understood to suggest that this predetermined level can be preselected, as by appropriate choice of resistor value at 18. FIG. 5 additionally shows a second annulus 15' of electro-optically sensitive properties. Annulus 15' is concentric with and surrounds annulus 15, the outer radius of 15 being substantially the inner radius of 15'. Further switch means 17' serves annulus 15', and it is shown connected for operation by a second phototransistor means 14', subject to such interlock of an enabling circuit element 23 as to assure that switch 17' will not turn on unless switch 17 has already turned on. The knob 22' at switch means 17' will be understood to suggest that a second light-intensity level may be preselected, below the level which will turn on switch means 17, thereby enabling the simulated pupil (in the FIG. 5 arrangement) to dilate to its widest in two steps, first via darkening area 15, and then via darkening area 15', as the phototransistors discern progressive diminishing of environmental light intensity. It is preferred that phototransistor 14 be mounted centrally as described in FIG. 1; phototransistor 14' may be immediately adjacent if small enough, but it may also be embedded in a sufficiently translucent foreign region of the sclera plastic 13, as will be understood.

The arrangement of FIGS. 6 and 7 applies the invention to a doll, wherein the pupils of the respective eyes are caused to dilate in unison, in response to decreasing light intensity. The basic operating electric components again are used with the same reference numbers, and the dilating-pupil annuli 15a and 15b for the respective eyes are shown connected in parallel to the output of switch means 17. Necessarily, there must be an electrical connection between eyes, i.e., external to each eye, and I prefer that the phototransistor means 14 be mounted externally of both eyes, as within the nose region 24 of the doll's head, this nose region being specially designed to be locally thin and translucent, to assure the described photo response. Heavy shading at 25 suggests preference for solidly potting the phototransistor means 14, the voltage source 16, transistor switch 17 and associated resistors within the nose region, relying upon a flexible-cable connection 26 therefrom to the respective eye elements 15a-15b.

The described forms of the invention will be seen to have met all stated objects. A new dimension in artificial-eye realism is thereby achieved, lending to the patient a substantially enhanced personal confidence (i.e., less chance of self-consciousness), in his dealings with others. In a typical employment, the phototransistor 14 is of Type CLT 2010, being a miniature product of Clairex Electronics, Mount Vernon, N.Y. Transistor switch 17 may be Clairex Type 2N 525, with resistors 18-19-20 having the values 2.7, 330, and 2.7 ohms respectively. Battery 16, as of the single-cell mercury type, has a 1.4 volt output. Of course, it will be understood that other commercially available miniature components may be used, including lithium cells for greater longevity. It will also be understood that the invention lends itself to a maximum utilization of existing techniques of artificial-eye fabrication, wherein a methylmethacrylate "button" with manipulating stud 10' (FIG. 1) provides the flat-bottom base on which liquid-crystal and indicia and component-bearing printed circuit means can be assembled, prior to the step of sclera molding to ultimate eye contour; any further finishing of the front surface of the eye would follow existing practice.

Figure 3B:
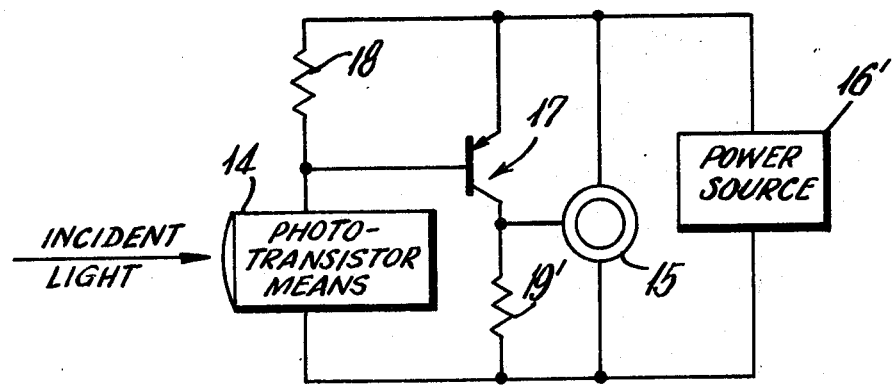

FIGS. 3A and 3B show further circuit embodiments using the components described in connection with FIG. 1, and of these, the embodiment of FIG. 3A is presently preferred. In FIG. 3A, a power source 16' will be understood to include battery 16 and to produce a pulsed or chopped rectangular-wave output, for a-c drive of a liquid-crystal display 15 which incorporates its drive circuitry. The phototransistor 14 may be Fairchild Type FPT-100, and transistor switch 17 may be Type 2N 2905, with the single resistor 18 having a value of 470 kilohms. The circuit of FIG. 3B is similar except that the liquid-crystal display 15 in FIG. 3B does not incorporate its drive circuitry and therefore an additional bias resistor 19' (suitably 68 kilohms) is employed to establish the light level at which switch 17 will be operative to change the transmitting vs. non-transmitting polarized state of the LCD display 15.

While the invention has been described in detail for a preferred form, it will be understood that modifications may be made without departing from the claimed scope of the invention. Thus, for example, the number of concentric rings at 15-15' etc. to progress the apparent dilation of the pupil may be three or more, giving the appearance of more smooth, rather than on-off, switching from small to large-pupil display.

What is claimed is:

1. An artificial eye, comprising a body with a front surface at which simulated sclera and iris indicia are directly viewable, a panel within said body at offset from said surface, said panel bearing the iris indicia on the side thereof facing said surface, said body being transparent at least in the front-surface region which registers with said iris indicia, said indicia including a central dark circular pupil-simulating region proportioned to simulate a pupil in a bright-light environment, photo-electric means having a light-sensitive element carried at said darkened region and facing said surface, an annular ring of electro-optically sensitive material in front of said iris indicia and concentrically surrounding said pupil-simulating region, the outer diameter of said ring being of a proportion to simulate the outer diameter of the pupil of a natural iris that has been dilated due to a light environment of intensity less than that of said bright environment, a voltage source contained by said body, and electric-switch means responsive to the voltage output of said photo-electric means and operative to connect said source into excitation relation with said electro-optically sensitive material for photoelectric output-voltage levels which are below a predetermined threshold level, whereby upon external viewing of said eye and for a sufficient change of environmental level of light intensity, the simulated pupil region will appear to dilate for a reduced intensity and to constrict for an increased intensity.

2. The artificial eye of claim 1, in which said body is a solid plastic potting with said panel and said photoelectric means and said electro-optical material and said switch means embedded therein.

3. An artificial eye, comprising a circuit board having a front surface bearing iris indicia characterized by a central dark circular area sized to simulate a pupil in a bright-light environment, said iris indicia further including an annular area surrounding the pupil-simulating area and colored and sized to simulate the remaining area of a simulated iris, a flat electro-optically sensitive annulus in front of said iris-simulating area and extending radially outward from said dark area to a radial extent to correspond with the outer diameter of a pupil that has been dilated due to light environment of intensity less than that of said bright environment, photoelectric means carried by said circuit board and having a sensitive element exposed to light incident upon said front surface, electric-circuit means carried by said board and so connecting said photoelectric means in operative relation with said electro-optically sensitive annulus as to cause excitation of said electro-optically sensitive annulus for photoelectric output-voltage levels which are below a predetermined voltage level, and eye-simulating body means mounting said circuit board and providing a transparent covering of at least said pupil-simulating region and providing a light-transmitting exposure of said photoelectric element.

4. The artificial eye of claim 3, in which said photoelectric element is at the dark central area.

5. The artificial eye of claim 3, in which said dark central area is provided by a hole in said circuit board.

6. The artificial eye of claim 3, in which said photoelectric means is a phototransistor.

7. The artificial eye of claim 3, in which said photoelectric means is a phototransistor having a front lens element sized and mounted to substantially determine said dark central area.

8. The artificial eye of claim 7, in which said body means includes a potting of transparent plastic material covering said iris indicia and in intimate covering adjacency with said lens.

9. The artificial eye of claim 8, in which said transparent potting is generally circular and in overstanding register with said pupil indicia, the remainder of said body means including a potting of sclera-simulating white plastic material in at least circumferentially continuous intimate surrounding adjacency with said transparent plastic material.

10. The artificial eye of claim 9, in which the potting of white plastic material is shaped to define with said transparent material the entire body of the eye with said board fully embedded therein.

11. The artificial eye of claim 3, in which said electric-circuit means includes a self-contained voltage source and electric-switch means connected for response to the output of said photoelectric means and controlling the application of source voltage to said electro-optically sensitive annulus.

12. The artificial eye of claim 11, in which said circuit board and all electrically connected components are fully potted in plastic material.

13. The artificial eye of claim 11, in which said voltage source is removably and replaceably mountable to said eye.

14. The artificial eye of claim 3, in which said flat electro-optically sensitive annulus is the inner one of a concentric plurality of such annuli in radially enlarged successive adjacency, the outer diameter of the largest annulus corresponding with the outer diameter of a fully dilated iris, said electric-circuit means so connecting said photoelectric means in operative relation with said respective annuli that successive larger annuli are caused to be excited for photoelectric output-voltage levels which are below successively lower predetermined voltage levels.

15. The artificial eye of claim 14, in which the number of said concentric annuli is two.

16. The artificial eye of claim 14, in which the number of said concentric annuli is three.

17. The artificial eye of claim 3, in which said electric-circuit means includes connecting means for acceptance of a remote voltage source to provide excitation voltage for said electro-optically sensitive annulus, and electric-switch means connected for response to the output of said photoelectric means for controlling the application of source voltage to said electro-optically sensitive annulus.

18. The artificial eye of claim 17, in which said connecting means includes a detachable connection.

19. The artificial eve of claim 17, in which said connecting means includes a flexible conductor.

20. The artificial eye of claim 3, in which said electro-optical annulus is of the liquid crystal display variety.

21. An artificial eye, comprising a substrate having a front surface bearing iris indicia characterized by a central dark circular area sized to simulate a pupil in a bright-light environment, said iris indicia further including an annular area surrounding the pupil-simulating area and colored and sized to simulate the remaining area of a simulated iris, a flat electro-optically sensitive annulus in front of said iris-simulating area and extending radially outward from said dark area to a radial extent to correspond with the outer diameter of a pupil that has been dilated due to a light environment of intensity less than that of said bright environment, electric-circuit means carried by said substrate with excitation connections to said electro-optically sensitive annulus, and eye-simulating body means mounting said substrate and providing a transparent covering of at least said pupil-simulating region.

22. The artificial eye of claim 21, and including photoelectric means remote from and flexibly connected to said circuit means and in such operative relation with said electro-optically sensitive annulus as to cause excitation of said electro-optically sensitive annulus for photoelectric output-voltage levels which are below a predetermined voltage level.

23. The artificial eye of claim 22, wherein said eye is one of two having concurrent parallel connection to said photoelectric means, whereby in application to a doll, the pupils of said eyes may be observed to dilate in unison in response to a reduction in environmental light.

24. The combination of claim 23, and including a doll's head with a face mounting said eyes, the doll's face including a region which is at least light-transmitting, said photoelectric means being mounted within said head for exposure adjacent said light-transmitting region.

25. The combination of claim 24, wherein said light-transmitting region is translucent.

26. An artificial eye comprising an eye-simulating body having a transparent covering of a dark circular pupil-simulating area within a surrounding annular iris-simulating area, the size of said circular area being such as to simulate a pupil in a bright-light environment, an electro-optically sensitive annulus interposed between said iris-simulating area and said transparent covering, said electro-optically sensitive annulus extending radially outward from said dark area to a radial extent to correspond with the outer diameter of a pupil that has been dilated due to a light environment of intensity less than that of said bright environment, and electric-circuit means carried by said body with excitation connections to said electro-optically sensitive annulus, said circuit means including photo-sensitive means having a light-sensitive element exposed through said transparent covering.

* * * * *